US012122842B1

(12) United States Patent
Munshi et al.

(10) Patent No.: US 12,122,842 B1
(45) Date of Patent: Oct. 22, 2024

(54) HUMAN CD30-SPECIFIC BINDING PROTEINS AND USES THEREOF

(71) Applicant: R&D Systems, Inc., Minneapolis, MN (US)

(72) Inventors: Cyrus B. Munshi, Minneapolis, MN (US); Kerri Ann Bostrom, Minneapolis, MN (US); Julie Anne Werner, Minneapolis, MN (US); Lori Ann Heitkamp, Minneapolis, MN (US)

(73) Assignee: R&D Systems, Inc., Minneapolis, MN (US)

( * ) Notice: Subject to any disclaimer, the term of this patent is extended or adjusted under 35 U.S.C. 154(b) by 0 days.

(21) Appl. No.: 18/475,892

(22) Filed: Sep. 27, 2023

(51) Int. Cl.
C07K 16/28 (2006.01)

(52) U.S. Cl.
CPC ...... *C07K 16/2878* (2013.01); *C07K 2317/24* (2013.01); *C07K 2317/33* (2013.01); *C07K 2317/92* (2013.01)

(58) Field of Classification Search
CPC ............ C07K 16/2878; C07K 2317/33; C07K 2317/92
See application file for complete search history.

(56) References Cited

U.S. PATENT DOCUMENTS

| | | | |
|---|---|---|---|
| 4,816,567 A | 3/1989 | Cabilly et al. | |
| 4,828,981 A | 5/1989 | Maggio | |
| 5,034,506 A | 7/1991 | Summerton et al. | |
| 5,480,792 A | 1/1996 | Buechler et al. | |
| 5,525,524 A | 6/1996 | Buechler et al. | |
| 5,679,526 A | 10/1997 | Buechler et al. | |
| 5,821,337 A | 10/1998 | Carter et al. | |
| 5,824,799 A | 10/1998 | Buechler et al. | |
| 5,851,776 A | 12/1998 | Valkirs | |
| 5,885,527 A | 3/1999 | Buechler | |
| 5,922,615 A | 7/1999 | Nowakowski et al. | |
| 5,939,272 A | 8/1999 | Buechler et al. | |
| 5,947,124 A | 9/1999 | Buechler et al. | |
| 5,985,579 A | 11/1999 | Buechler et al. | |
| 6,019,944 A | 2/2000 | Buechler | |
| 6,113,855 A | 9/2000 | Buechler | |
| 6,143,576 A | 11/2000 | Buechler | |
| 6,248,516 B1 | 6/2001 | Winter et al. | |
| 6,982,321 B2 | 1/2006 | Winter | |
| 7,087,409 B2 | 8/2006 | Barbas, III et al. | |
| 7,527,791 B2 | 5/2009 | Adams et al. | |
| 8,568,992 B2 | 10/2013 | Walker et al. | |
| 2001/0021516 A1 | 9/2001 | Wei et al. | |
| 2004/0006215 A1* | 1/2004 | Keler | C07K 16/2878 530/388.22 |
| 2022/0144960 A1 | 5/2022 | Yang et al. | |

FOREIGN PATENT DOCUMENTS

| EP | 0404097 | 9/1996 |
|---|---|---|
| WO | WO 1993/01161 | 1/1993 |
| WO | WO 1997/10003 | 3/1997 |

OTHER PUBLICATIONS de Marco A. Recombinant expression of nanobodies and nanobody-derived immunoreagents. Protein Expr Purif. Aug. 2020;172:105645. doi: 10.1016/j.pep.2020.105645. Epub Apr. 11, 2020. PMID: 32289357; PMCID: PMC7151424. (Year: 2020).*

Muyldermans S. A guide to: generation and design of nanobodies. FEBS J. Apr. 2021;288(7):2084-2102. doi: 10.1111/febs.15515. Epub Aug. 28, 2020. PMID: 32780549; PMCID: PMC8048825. (Year: 2021).*

Muyldermans S. Applications of Nanobodies. Annu Rev Anim Biosci. Feb. 16, 2021;9:401-421. doi: 10.1146/annurev-animal-021419-083831. Epub Nov. 24, 2020. PMID: 33233943. (Year: 2021).*

Sela-Culang I, Kunik V, Ofran Y. The structural basis of antibody-antigen recognition. Front Immunol. Oct. 8, 2013;4:302. doi:10.3389/fimmu.2013.00302. PMID: 24115948; PMCID: PMC3792396. (Year: 2013).*

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. doi: 10.4049/jimmunol.165.8.4505. PMID: 11035090. (Year: 2000).*

Gruss HJ, Boiani N, Williams DE, Armitage RJ, Smith CA, Goodwin RG. Pleiotropic effects of the CD30 ligand on CD30-expressing cells and lymphoma cell lines. Blood. Apr. 15, 1994;83(8):2045-56. PMID: 8161776. (Year: 1994).*

Wahl AF et al. The anti-CD30 monoclonal antibody SGN-30 promotes growth arrest and DNA fragmentation in vitro and affects antitumor activity in models of Hodgkin's disease. Cancer Res. Jul. 1, 2002;62(13):3736-42. PMID: 12097283. (Year: 2002).*

Van Meerten T, Hagenbeek A. Novel antibodies against follicular non-Hodgkin's lymphoma. Best Pract Res Clin Haematol. Jun. 2011;24(2):231-56. doi: 10.1016/j.beha.2011.03.002. Epub May 5, 2011. PMID: 21658621. (Year: 2011).*

Adamczyk et al., Homogeneous chemiluminescent assays for free choline in human plasma and whole blood. Anal Chim Acta. Oct. 2, 2006;579(1):61-7.

Almagro et al., Humanization of antibodies. Front Biosci. Jan. 1, 2008;13:1619-33.

Altschul et al., Basic local alignment search tool. J Mol Biol. Oct. 5, 1990;215(3):403-10.

Altschul et al., Gapped Blast and PSI-Blast: a new generation of protein database search programs. Nucleic Acids Res. Sep. 1, 1997;25(17):3389-402.

Ausubel et al., Current Protocols in Molecular Biology, Greene Publishing Associates and John Wiley & Sons, New York, N.Y. 1994. TOC only. 14 pages.

(Continued)

*Primary Examiner* — Julie Wu
*Assistant Examiner* — Carol Ann Chase
(74) *Attorney, Agent, or Firm* — Casimir Jones, S.C.; Peter J. Schlueter

(57) ABSTRACT

Embodiments of the present disclosure relate to antigen-binding affinity reagents for an analyte-of-interest. In particular, the present disclosure provides novel binding proteins (antibodies), including derivatives and fragments thereof, that target human CD30.

10 Claims, 3 Drawing Sheets

Figure 1:
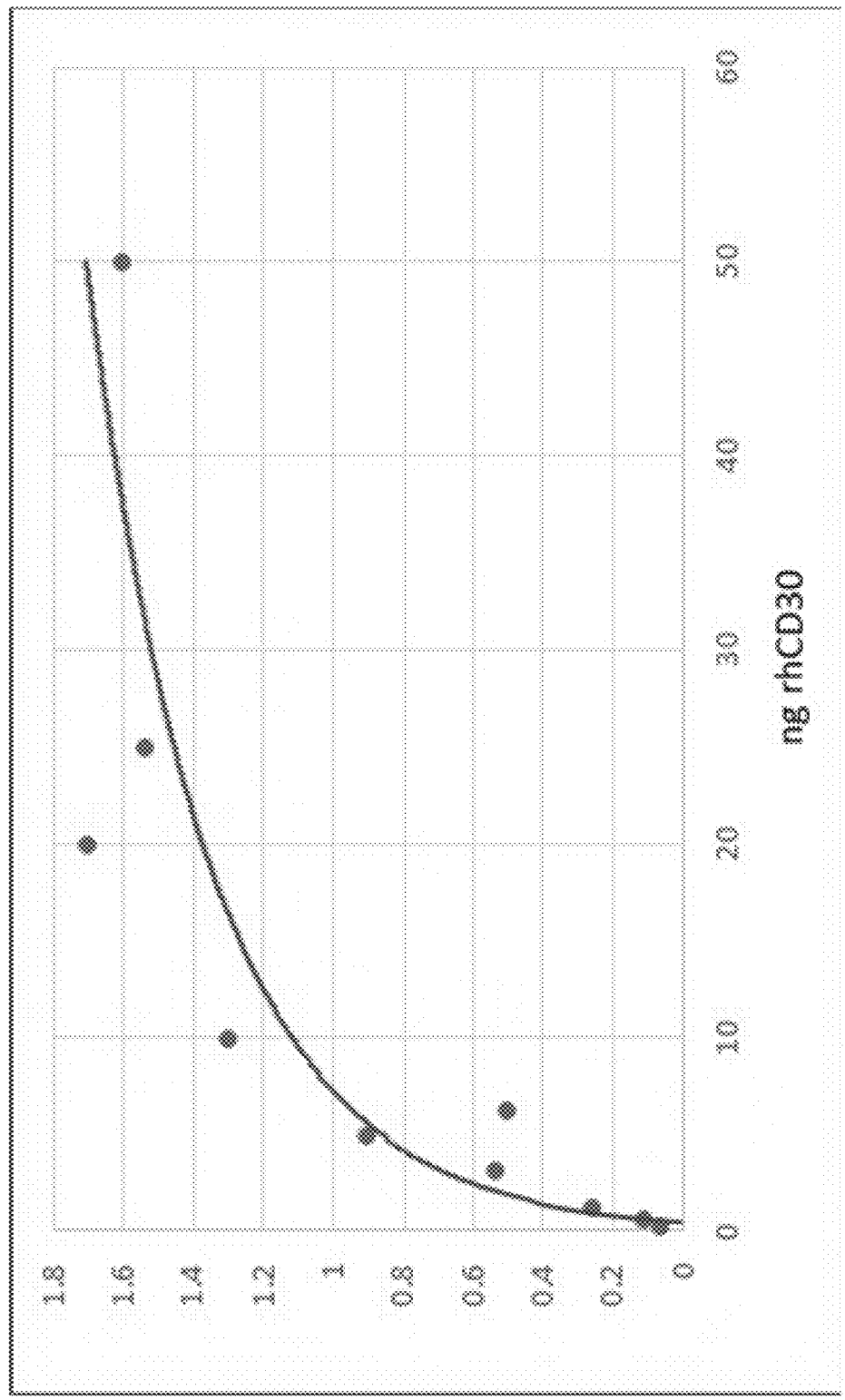

Specification includes a Sequence Listing.

(56) References Cited

OTHER PUBLICATIONS

Ausubel et al., eds., Short Protocols in Molecular Biology, 5th ed., John Wiley & Sons, Inc., Hoboken, N.J. 2002. TOC only. 20 pages.
Bates et al., David vs. Goliath: The Structure, Function, and Clinical Prospects of Antibody Fragments. Antibodies (Basel). Apr. 9, 2019;8(2):28. 31 pages.
Beigert et al., Sequence context-specific profiles for homology searching. PNAS. Mar. 10, 2009. 106(10), 3770-3775.
Braasch et al., Novel antisense and peptide nucleic acid strategies for controlling gene expression. Biochemistry. Apr. 9, 2002;41(14):4503-10.
Braitbard et al., Competition between bound and free peptides in an ELISA-based procedure that assays peptides derived from protein digests. Proteome Sci. May 31, 2006:4:12. 1-14.
Chothia et al., Canonical structures for the hypervariable regions of immunoglobulins. J Mol Biol. Aug. 20, 1987;196(4):901-17.
Clackson et al., Making antibody fragments using phage display libraries. Nature. Aug. 15, 1991;352(6336):624-8.
Dall'Acqua et al., Antibody humanization by framework shuffling. Methods. May 2005;36(1):43-60.
Dall'Acqua et al., Increasing the affinity of a human IgG1 for the neonatal Fc receptor: biological consequences. J Immunol. Nov. 1, 2002;169(9):5171-80.
Durbin et al., eds., Biological Sequence Analysis: Probabilistic Models of Proteins and Nucleic Acids, Cambridge University Press, Cambridge, UK, 2002. TOC only. 7 pages.
Goeddel, Gene Expression Technology: Methods in Enzymology, vol. 185, Academic Press, San Diego, Calif. 1990. TOC only. 7 pages.
Gusfield, Algorithms on Strings, Trees and Sequences, Cambridge University Press, Cambridge UK. 1997. TOC only. 8 pages.
Holliger et al., "Diabodies": small bivalent and bispecific antibody fragments. Proc Natl Acad Sci U S A. Jul. 15, 1993;90(14):6444-8.
Holliger et al., Engineered antibody fragments and the rise of single domains. Nat Biotechnol. Sep. 2005;23(9):1126-36.
Hudson et al., Engineered antibodies. Nat Med. Jan. 2003;9(1):129-34.
Janeway et al. (eds.), Immunobiology, 5th Ed., Garland Publishing, New York, N.Y. 2001. TOC only. 41 pages.
Joosten et al., The production of antibody fragments and antibody fusion proteins by yeasts and filamentous fungi. Microbial Cell Factories. 2003, 2:1, 15 pages.
Kabat et al., Sequences of Proteins of Immunological Interest, Fifth Edition, U.S. Department of Health and Human Services, NIH Publication No. 91-3242, 1991. TOC only. 11 pages.
Kang et al., Boosting therapeutic potency of antibodies by taming Fc domain functions. Exp Mol Med. Nov. 18, 2019;51(11):1-9.
Kashmiri et al., SDR grafting—a new approach to antibody humanization. Methods. May 2005;36(1):25-34.
Kennedy et al., Deciphering CD30 ligand biology and its role in humoral immunity. Immunology. Jun. 2006;118(2):143-52.
Kitts et al., A method for producing recombinant baculovirus expression vectors at high frequency. Biotechniques. May 1993;14(5):810-7.
Klimka et al., Human anti-CD30 recombinant antibodies by guided phage antibody selection using cell panning. Br J Cancer. Jul. 2000;83(2):252-60.
Kohler et al., Derivation of specific antibody-producing tissue culture and tumor lines by cell fusion. Eur J Immunol. Jul. 1976;6(7):511-9.
Lazar et al., Engineered antibody Fc variants with enhanced effector function. Proc Natl Acad Sci U S A. Mar. 14, 2006;103(11):4005-10.
Lehninger, Principles of Biochemistry, Worth Pub. 1982. 793-800.
Li et al., Modulating IgG effector function by Fc glycan engineering. Proc Natl Acad Sci U S A. Mar. 28, 2017;114(13):3485-3490.
Lin et al., A common glycan structure on immunoglobulin G for enhancement of effector functions. Proc Natl Acad Sci U S A. Aug. 25, 2015;112(34):10611-6.

Liu et al., Asymmetrical Fc engineering greatly enhances antibody-dependent cellular cytotoxicity (ADCC) effector function and stability of the modified antibodies. J Biol Chem. Feb. 7, 2014;289(6):3571-90.
Lonberg. Human antibodies from transgenic animals. Nat Biotechnol. Sep. 2005;23(9):1117-25.
Lonberg. Human monoclonal antibodies from transgenic mice. Handb Exp Pharmacol. 2008;181(181):69-97.
Luckow et al., Efficient generation of infectious recombinant baculoviruses by site-specific transposon-mediated insertion of foreign genes into a baculovirus genome propagated in *Escherichia coli*. J Virol. Aug. 1993;67(8):4566-79.
Luckow. Baculovirus systems for the expression of human gene products. Curr Opin Biotechnol. Oct. 1993;4(5):564-72.
Marks et al., By-passing immunization. Human antibodies from V-gene libraries displayed on phage. J Mol Biol. Dec. 5, 1991;222(3):581-97.
Mimoto et al., Fc Engineering to Improve the Function of Therapeutic Antibodies. Curr Pharm Biotechnol. 2016;17(15):1298-1314.
Monnet et al., Combined glyco- and protein-Fc engineering simultaneously enhance cytotoxicity and half-life of a therapeutic antibody. MAbs. Mar.-Apr. 2014;6(2):422-36.
Monnier et al., In Vivo Applications of Single Chain Fv (Variable Domain) (scFv) Fragments. Antibodies. 2013, 2, 193-208.
Morrison et al., Chimeric human antibody molecules: mouse antigen-binding domains with human constant region domains. Proc Natl Acad Sci U S A. Nov. 1984;81(21):6851-5.
Nelson. Antibody fragments: hope and hype. MAbs. Jan.-Feb. 2010;2(1):77-83.
Nordstrom et al., Anti-tumor activity and toxicokinetics analysis of MGAH22, an anti-HER2 monoclonal antibody with enhanced Fcγ receptor binding properties. Breast Cancer Res. 2011;13(6):R123.
Osbourn et al., From rodent reagents to human therapeutics using antibody guided selection. Methods. May 2005;36(1):61-8.
Padlan. A possible procedure for reducing the immunogenicity of antibody variable domains while preserving their ligand-binding properties. Mol Immunol. Apr.-May 1991;28(4-5):489-98.
Queen et al., A humanized antibody that binds to the interleukin 2 receptor. Proc Natl Acad Sci U S A. Dec. 1989;86(24):10029-33.
Richards et al., Optimization of antibody binding to FcgammaRIIa enhances macrophage phagocytosis of tumor cells. Mol Cancer Ther. Aug. 2008;7(8):2517-27.
Riechmann et al., Reshaping human antibodies for therapy. Nature. Mar. 24, 1988;332(6162):323-7.
Safdari et al., Use of single chain antibody derivatives for targeted drug delivery. Mol Med. Sep. 2016:22:258-270.
Sambrook et al., Molecular Cloning, a Laboratory Manual, Cold Spring Harbor Press, Cold Spring Harbor, N.Y. 2001. TOC only. 23 pages.
Saunders et al., Conceptual Approaches to Modulating Antibody Effector Functions and Circulation Half-Life. Front Immunol. Jun. 7, 2019:10:1296. 20 pages.
Schulz and Schirmer, Principles of Protein Structure, Springer-Verlag, New York. 1979. TOC only. 11 pages.
Soding. Protein homology detection by HMM-HMM comparison. Bioinformatics. Apr. 1, 2005;21(7):951-60.
Urlaub et al., Isolation of Chinese hamster cell mutants deficient in dihydrofolate reductase activity. Proc Natl Acad Sci U S A. Jul. 1980;77(7):4216-20.
Vidarsson et al., IgG subclasses and allotypes: from structure to effector functions. Front Immunol. Oct. 20, 2014:5:520. 17 pages.
Wahlestedt et al., Potent and nontoxic antisense oligonucleotides containing locked nucleic acids. Proc Natl Acad Sci U S A. May 9, 2000;97(10):5633-8.
Wang et al., Cyclohexene Nucleic Acids (CeNA): Serum Stable Oligonucleotides that Activate RNase H and Increase Duplex Stability with Complementary RNA. J. Am. Chem. Soc. 2000, 122, 36, 8595-8602.
Zalevsky et al., Enhanced antibody half-life improves in vivo activity. Nat Biotechnol. Feb. 2010;28(2):157-9.
X59115, European Nucleotide Archive Accession No. X59115, M.musculus mRNA (L20-5G3) for IgH heavy chain V region, Jan. 6, 1995. On line. Retrieved Jan. 3, 2024. 1 page.

(56) References Cited

OTHER PUBLICATIONS

International Search Report and Written Opinion for PCT/US23/75241. Mailed Feb. 21, 2024. 12 pages.

* cited by examiner

HUMAN CD30-SPECIFIC BINDING PROTEINS AND USES THEREOF

SEQUENCE LISTING

The text of the computer readable sequence listing filed herewith, titled "BIOTN_42419_151_SequenceListing", created Sep. 25, 2023, having a file size of 274,522 bytes, is hereby incorporated by reference in its entirety.

FIELD

Embodiments of the present disclosure relate to antigen-binding affinity reagents for an analyte-of-interest. In particular, the present disclosure provides novel binding proteins (e.g., antibodies), including derivatives and fragments thereof, that target CD30.

BACKGROUND

CD30, also known as Ki-1 antigen and TNFRSF8, is a 120 kDa type I transmembrane glycoprotein belonging to the TNF receptor superfamily (Kennedy et al., 2006, *Immunology* 118:143-152). Mature human CD30 (hCD30) consists of a 361 amino acid (aa) extracellular domain (ECD) with six cysteine-rich repeats, a 28 aa transmembrane segment, and a 188 aa cytoplasmic domain. In contrast, mouse and rat CD30 molecules lack 90 aa of the ECD and contain only three cysteine-rich repeats. Within common regions of the ECD, human CD30 shares 53% and 49% aa sequence identity with mouse and rat CD30, respectively. Alternate splicing of human CD30 generates an isoform that includes only the C-terminal 132 aa of the cytoplasmic domain. CD30 is normally expressed on antigen-stimulated T-helper (Th) cells and B cells. CD30 contributes to thymic negative selection by inducing the apoptotic cell death of CD4+CD8+ T cells. In B cells, CD30 ligation promotes cellular proliferation and antibody production in addition to the expression of CXCR4, CCL3, and CCL5. An 85-90 kilodalton (kDa) soluble form of CD30 is shed from the cell surface by tumor necrosis factor-α-converting enzyme (TACE)-mediated cleavage. Soluble CD30 retains the ability to bind CD30 ligand and functions as an inhibitor of normal CD30 signaling.

SUMMARY

Embodiments of the present disclosure include a binding protein directed against human CD30. In accordance with these embodiments, the binding protein comprises a heavy chain variable region ($V_H$) comprising complementarity determining regions (CDRs) HCDR1, HCDR2, and HCDR3, wherein the HCDR1 comprises SEQ ID NO: 1, the HCDR2 comprises SEQ ID NO: 2, and the HCDR3 comprises SEQ ID NO: 3. In some embodiments, the $V_H$ region comprises SEQ ID NO: 7.

In some embodiments, the binding protein is selected from the group consisting of: a monoclonal antibody, a human antibody, a humanized antibody, a single-domain antibody, and a chimeric antibody.

In some embodiments, the binding protein comprises an antibody fragment selected from the group consisting of Fab, Fab-C, Fab'-SH, Fv, scFv, (Fab')$_2$, and VHH.

In some embodiments, the antibody binds hCD30 ligand/TNFSF8.

In some embodiments, the binding protein is an antibody, or an antigen-binding fragment thereof, and further comprises a light chain variable region ($V_L$) comprising complementarity determining regions (CDRs) LCDR1, LCDR2, and LCDR3, and wherein the LCDR1 comprises SEQ ID NO: 4, the LCDR2 comprises SEQ ID NO: 5, the LCDR3 comprises SEQ ID NO: 6. In some embodiments, the $V_L$ region comprises SEQ ID NO: 8.

In some embodiments, the binding protein binds hCD30 with a $K_D$ of about 5.1 nM or lower.

In some embodiments, the binding protein does not cross-react with mouse CD30 (mCD30).

In some embodiments, the binding protein comprises a detection moiety or a purification moiety.

In some embodiments, the binding protein binds an epitope from a hCD30 polypeptide having an amino acid sequence of SEQ ID NO: 9 corresponding to hCD30 isoform 1 (Uniprot Accession No. P28908-1); SEQ ID NO: 10 corresponding to hCD30 isoform 2 (Uniprot Accession No. P28908-2); and/or SEQ ID NO: 11 corresponding to hCD30 isoform 3 (Uniprot Accession No. P28908-3).

Embodiments of the present disclosure also include a composition comprising any of the binding protein described herein. In some embodiments, the binding protein is an antibody, or an antigen-binding fragment thereof, and the composition comprises (i) a mixture of identical antibodies, or (ii) a mixture of different antibodies.

Embodiments of the present disclosure also include a polynucleotide comprising a nucleic acid sequence encoding any of the binding proteins described here.

BRIEF DESCRIPTION OF THE DRAWING(S)

FIG. 1: Direct ELISA results of recombinant hCD30 antibody.

Figure 2:
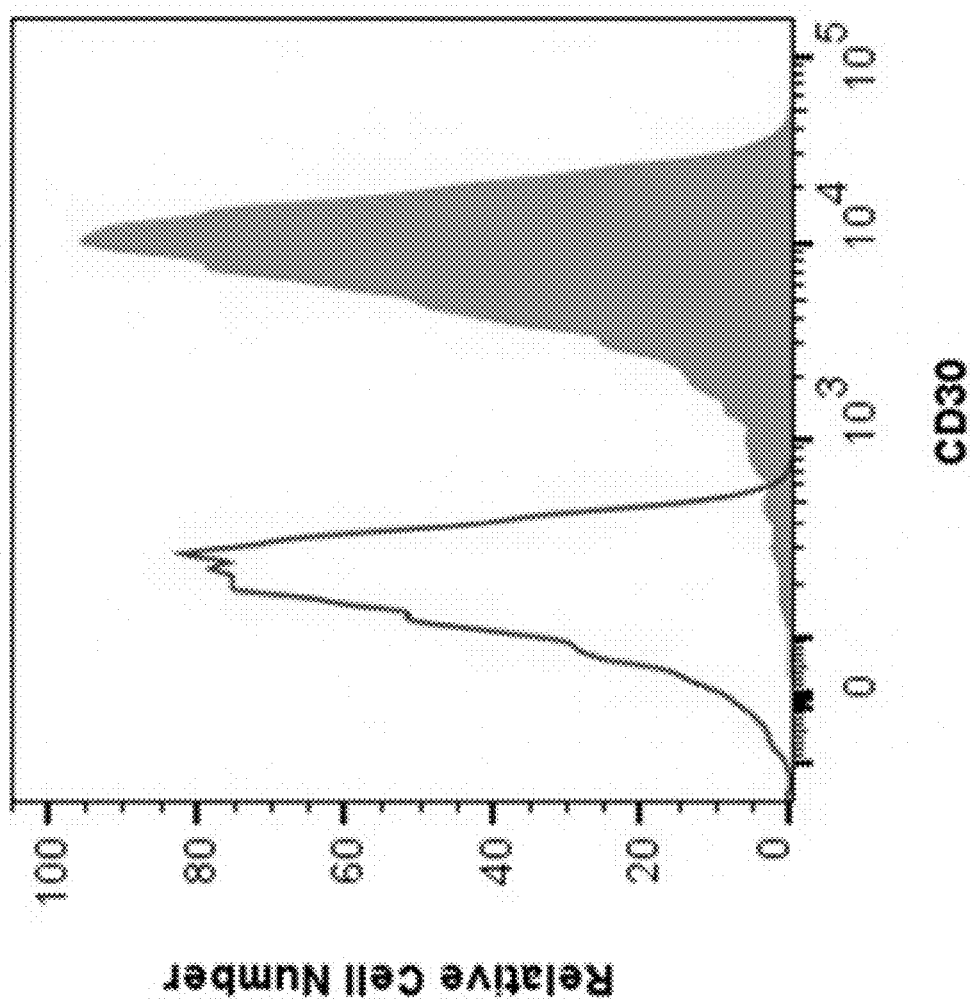

FIG. 2: Detection of hCD30/TNFRSF8 in Jurkat human cell line by flow cytometry. Jurkat human acute T cell leukemia cell line (Clone E6-1, ATCC Catalog #TIB-152) was stained with Mouse Anti-Human CD30 Monoclonal Antibody (Clone 81316.11, filled histogram) or isotype control antibody (Catalog #MAB002, open histogram), followed by Phycoerythrin-conjugated Anti-Mouse IgG Secondary Antibody (Catalog #F0102B).

Figure 3:
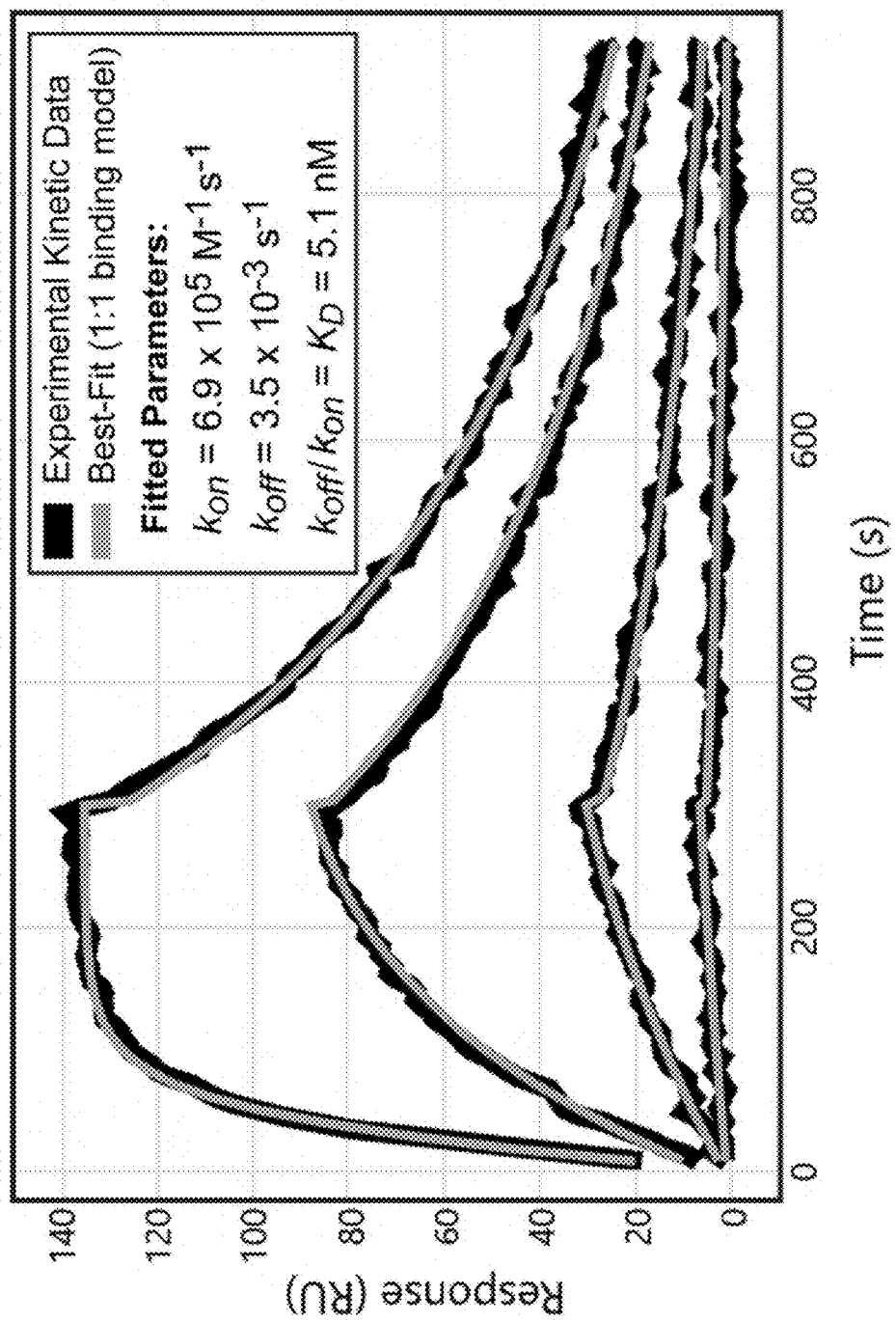

FIG. 3: Surface plasmon resonance binding of the anti-hCD30 antibody (employed here as the surface immobilized ligand) to recombinant hCD30 protein (employed here as the solution phase analyte).

DETAILED DESCRIPTION

Embodiments of the present disclosure relate to antigen-binding affinity reagents for an analyte-of-interest, including but not limited to, a peptide, polypeptide, protein, amino acid, nucleic acid, polynucleotide, small molecule, lipid, carbohydrate, cell, organelle, etc. In particular, the present disclosure provides novel binding proteins (e.g., antibodies), including derivatives and fragments thereof, that target human CD30, which is involved in TNF/TNF ligand superfamily-related pathways.

CD30, also known as Ki-1 antigen and TNFRSF8, is a 120 kDa type I transmembrane glycoprotein belonging to the TNF receptor superfamily. Mature human CD30 consists of a 361 amino acid (aa) extracellular domain (ECD) with six cysteine-rich repeats, a 28 aa transmembrane segment, and a 188 aa cytoplasmic domain. In contrast, mouse and rat CD30 molecules lack 90 aa of the ECD and contain only three cysteine-rich repeats. Within common regions of the ECD, hCD30 shares 53% and 49% aa sequence identity with mouse and rat CD30, respectively. Alternate splicing of hCD30 generates an isoform that includes only the C-terminal 132 aa of the cytoplasmic domain. hCD30 is normally expressed on antigen-stimulated Th cells and B cells. CD30 binds to CD30 ligand/TNFSF8 which is expressed on activated Th cells, monocytes, granulocytes and medullary thymic epithelial cells. CD30 signaling co-stimulates antigen-induced Th0 and Th2 proliferation and cytokine secretion but favors a Th2-biased immune response. In the absence of antigenic stimulation, CD30 can still induce T cell expression of IL-13. CD30 contributes to thymic negative selection by inducing the apoptotic cell death of CD4+ CD8+ T cells. In B cells, CD30 ligation promotes cellular proliferation and antibody production in addition to the expression of CXCR4, CCL3, and CCL5. An 85-90 kDa soluble form of CD30 is shed from the cell surface by TACE-mediated cleavage. Soluble CD30 retains the ability to bind CD30 ligand and functions as an inhibitor of normal CD30 signaling. The protein encoded by this gene is a member of the TNF-receptor superfamily. This receptor is expressed by activated, but not by resting, T and B cells. TRAF2 and TRAF5 can interact with this receptor, and mediate the signal transduction that leads to the activation of NF-κB. Two alternatively spliced transcript variants of this gene encoding distinct isoforms have been reported.

Definitions

To facilitate an understanding of the present technology, a number of terms and phrases are defined below. Additional definitions are set forth throughout the detailed description.

The term "analyte" generally refers to any molecule, compound, or substance that can be bound by one or more of the of the present disclosure. An analyte that can be bound by the antigen-binding affinity reagents of the present disclosure includes, but is not limited to, a peptide, polypeptide, protein, amino acid, nucleic acid, polynucleotide, small molecule, lipid, carbohydrate, cell, organelle, etc. In some cases, an analyte exhibits antigenic and/or immunogenic properties in a subject; however, in other cases, an analyte does not exhibit any known antigenic and/or immunogenic properties.

The terms "affinity reagent" and "antigen-binding affinity reagent" as used herein generally refer to a binding protein or polypeptide containing one or more domains that bind an epitope or antigen of an analyte, where such domains are derived from, or have some degree of sequence identity with, a variable region of an antibody. The antibody can be a naturally-occurring antibody, a synthetic antibody, or a design engineered antibody. Typically, an immunoglobulin or antibody is a protein that comprises at least one complementarity determining region (CDR). The CDRs form the "hypervariable region" of an antibody, which is responsible for antigen binding (discussed further below). A whole antibody typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($C_{H1}$, $C_{H2}$, and $C_{H3}$) regions, and each light chain contains one N-terminal variable ($V_L$) region and one C-terminal constant ($C_L$) region. The light chains of antibodies can be assigned to one of two distinct types, either kappa (κ) or lambda (λ), based upon the amino acid sequences of their constant domains. In a typical antibody, each light chain is linked to a heavy chain by disulfide bonds, and the two heavy chains are linked to each other by disulfide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen-binding site of an antibody. The $V_H$ and $V_L$ regions have the same general structure, with each region comprising four framework (FW or FR) regions. The term "framework region," as used herein, refers to the relatively conserved amino acid sequences within the variable region which are located between the CDRs. There are four framework regions in each variable domain, which are designated FR1, FR2, FR3, and FR4. The framework regions form the R sheets that provide the structural framework of the variable region (see, e.g., C. A. Janeway et al. (eds.), Immunobiology, 5th Ed., Garland Publishing, New York, N.Y. (2001)).

The framework regions are connected by three CDRs. As discussed above, the three CDRs, known as CDR1, CDR2, and CDR3, form the "hypervariable region" of an antibody, which is responsible for antigen binding. The CDRs form loops connecting, and in some cases comprising part of, the beta-sheet structure formed by the framework regions. While the constant regions of the light and heavy chains are not directly involved in binding of the antibody to an antigen, the constant regions can influence the orientation of the variable regions. The constant regions also exhibit various effector functions, such as participation in antibody-dependent complement-mediated lysis or antibody-dependent cellular toxicity via interactions with effector molecules and cells.

The extent of the FRs and CDRs has been precisely defined (see, Kabat et al. (1991) Sequences of Proteins of Immunological Interest, Fifth Edition, U.S. Department of Health and Human Services, NIH Publication No. 91-3242, and (Chothia et al. *J Mol Biol* 196, 901-917 (1987))). Each $V_H$ and $V_L$ is composed of three CDRs and four FRs, arranged from amino-terminus to carboxy-terminus in the following order: FR1, CDR1, FR2, CDR2, FR3, CDR3, FR4. Annotation of the FRs and CDRs was performed using the Kabat numbering scheme. Using this model, amino acid sequences of the variable region of the light (λ, κ) and heavy chain of antibodies, as well as the variable region of T cell receptors (α, β, γ, δ) were aligned and numbered.

As used herein, when an antibody or other entity (e.g., antigen binding domain) "specifically recognizes" or "specifically binds" an antigen or epitope, it preferentially recognizes the antigen in a complex matrices mixture of proteins and/or macromolecules (e.g., biological samples, soil samples, water samples, biomanufacturing feed streams, industrial samples, and the like), and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7$ $M^{-1}$, $>10^8$ $M^{-1}$, $>10^9$ $M^{-1}$, $>10^{10}$ $M^{-1}$, $>10^{11}$ $M^{-1}$, $>10^{12}$ $M^{-1}$, $>10^{13}$ $M^{-1}$, etc.). In certain such embodiments, an antibody is capable of binding different antigens so long as the different antigens comprise that particular epitope. In certain instances, for example, homologous proteins from different species may comprise the same epitope.

The terms "fragment of an antibody," "antibody fragment," and "antigen-binding fragment" of an antibody are used interchangeably herein to refer to one or more fragments of an antibody that retain the ability to specifically bind to an antigen (see, generally, Holliger et al., *Nat. Biotech.*, 23(9): 1126-1129 (2005)). Any antigen-binding fragment of the antibody described herein is within the scope of the present disclosure. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the $V_L$, $V_H$, $C_L$, and $C_{H1}$ domains, (ii) a F(ab')2 fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an F(ab')2 fragment using mild reducing conditions, (v) a disulfide-stabilized Fv fragment (dsFv), and (vi) a domain antibody (dAb), which is an antibody single variable region domain ($V_H$ or $V_L$) polypeptide that specifically binds antigen.

The term "monoclonal antibody," as used herein, refers to an antibody produced by a single clone of B lymphocytes that is directed against a single epitope on an antigen. Monoclonal antibodies typically are produced using hybridoma technology, as first described in Kohler and Milstein, *Eur. J. Immunol.*, 5: 511-519 (1976). Monoclonal antibodies may also be produced using recombinant DNA methods (see, e.g., U.S. Pat. No. 4,816,567), isolated from phage display antibody libraries (see, e.g., Clackson et al. *Nature*, 352: 624-628 (1991)); and Marks et al., *J. Mol. Biol.*, 222: 581-597 (1991)), or produced from transgenic mice carrying a fully human immunoglobulin system (see, e.g., Lonberg, *Nat. Biotechnol.*, 23(9): 1117-25 (2005), and Lonberg, *Handb. Exp. Pharmacol.*, 181: 69-97 (2008)). In contrast, "polyclonal" antibodies are mixtures of antibodies that are secreted by different B cell lineages within an animal. Polyclonal antibodies are a collection of immunoglobulin molecules that recognize multiple epitopes on the same antigen.

The terms "nucleic acid," "polynucleotide," "nucleotide sequence," and "oligonucleotide" are used interchangeably herein and refer to a polymer or oligomer of pyrimidine and/or purine bases, preferably cytosine, thymine, and uracil, and adenine and guanine, respectively (See Albert L. Lehninger, *Principles of Biochemistry*, at 793-800 (Worth Pub. 1982)). The terms encompass any deoxyribonucleotide, ribonucleotide, or peptide nucleic acid component, and any chemical variants thereof, such as methylated, hydroxymethylated, or glycosylated forms of these bases. The polymers or oligomers may be heterogenous or homogenous in composition, may be isolated from naturally occurring sources, or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. In some embodiments, a nucleic acid or nucleic acid sequence comprises other kinds of nucleic acid structures such as, for instance, a DNA/RNA helix, peptide nucleic acid (PNA), morpholino nucleic acid (see, e.g., Braasch and Corey, *Biochemistry*, 41(14): 4503-4510 (2002) and U.S. Pat. No. 5,034,506), locked nucleic acid (LNA; see Wahlestedt et al., *Proc. Natl. Acad. Sci. U.S.A.*, 97: 5633-5638 (2000)), cyclohexenyl nucleic acids (see Wang, *J. Am. Chem. Soc.*, 122: 8595-8602 (2000)), and/or a ribozyme. The terms "nucleic acid" and "nucleic acid sequence" may also encompass a chain comprising non-natural nucleotides, modified nucleotides, and/or non-nucleotide building blocks that can exhibit the same function as natural nucleotides (e.g., "nucleotide analogs").

The terms "peptide," "polypeptide," and "protein" are used interchangeably herein and refer to a polymeric form of amino acids of any length, which can include coded and non-coded amino acids, chemically or biochemically modified or derivatized amino acids, and polypeptides having modified peptide backbones.

The terms "immunogen" and "antigen" are used interchangeably herein and refer to any molecule, compound, or substance that induces an immune response in an animal (e.g., a mammal). An "immune response" can entail, for example, antibody production and/or the activation of immune effector cells. An antigen in the context of the disclosure can comprise any subunit, fragment, or epitope of any proteinaceous or non-proteinaceous (e.g., carbohydrate or lipid) molecule that provokes an immune response in a mammal. The term "epitope" means a sequence of an antigen that is recognized by an antibody or an antigen receptor. Epitopes also are referred to in the art as "antigenic determinants." In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three-dimensional structural characteristics (e.g., a "conformational" epitope) and/or specific charge characteristics. The antigen can be a protein or peptide of viral, bacterial, parasitic, fungal, protozoan, prion, cellular, or extracellular origin, which provokes an immune response in a mammal, preferably leading to protective immunity.

Anti-hCD30 Antibodies

The present disclosure includes an antibody directed against hCD30 peptides, or an antigen-binding fragment thereof, comprising a heavy chain variable region ($V_H$) comprising complementarity determining regions (CDRs) HCDR1, HCDR2, and HCDR3, and a light chain variable region ($V_L$) comprising complementarity determining regions (CDRs) LCDR1, LCDR2, and LCDR3. In some embodiments, the HCDR1 comprises SEQ ID NO: 1, the HCDR2 comprises SEQ ID NO: 2, the HCDR1 comprises SEQ ID NO: 3, the LCDR1 comprises SEQ ID NO: 4, the LCDR2 comprises SEQ ID NO: 5, the LCDR3 comprises SEQ ID NO: 6.

In some embodiments, the $V_H$ comprises an amino acid sequence that is at least 90% identical to SEQ ID NO: 7. In some embodiments, the $V_H$ comprises an amino acid sequence that is at least 91% identical to SEQ ID NO: 7. In some embodiments, the $V_H$ comprises an amino acid sequence that is at least 92% identical to SEQ ID NO: 7. In some embodiments, the $V_H$ comprises an amino acid sequence that is at least 93% identical to SEQ ID NO: 7. In some embodiments, the $V_H$ comprises an amino acid sequence that is at least 94% identical to SEQ ID NO: 7. In some embodiments, the $V_H$ comprises an amino acid sequence that is at least 95% identical to SEQ ID NO: 7. In some embodiments, the $V_H$ comprises an amino acid sequence that is at least 96% identical to SEQ ID NO: 7. In some embodiments, the $V_H$ comprises an amino acid sequence that is at least 97% identical to SEQ ID NO: 7. In some embodiments, the $V_H$ comprises an amino acid sequence that is at least 98% identical to SEQ ID NO: 7. In some embodiments, the $V_H$ comprises an amino acid sequence that is at least 99% identical to SEQ ID NO: 7. In some embodiments, the $V_H$ comprises an amino acid sequence that is 100% identical to SEQ ID NO: 7.

In some embodiments, the $V_L$ comprises an amino acid sequence that is at least 90% identical to SEQ ID NO: 8. In some embodiments, the $V_L$ comprises an amino acid sequence that is at least 91% identical to SEQ ID NO: 8. In some embodiments, the $V_L$ comprises an amino acid sequence that is at least 92% identical to SEQ ID NO: 8. In some embodiments, the $V_L$ comprises an amino acid sequence that is at least 93% identical to SEQ ID NO: 8. In some embodiments, the $V_H$ comprises an amino acid sequence that is at least 94% identical to SEQ ID NO: 8. In some embodiments, the $V_L$ comprises an amino acid sequence that is at least 95% identical to SEQ ID NO: 8. In some embodiments, the $V_L$ comprises an amino acid sequence that is at least 96% identical to SEQ ID NO: 8. In some embodiments, the $V_L$ comprises an amino acid sequence that is at least 97% identical to SEQ ID NO: 8. In some embodiments, the $V_L$ comprises an amino acid sequence that is at least 98% identical to SEQ ID NO: 8. In some embodiments, the $V_L$ comprises an amino acid sequence that is at least 99% identical to SEQ ID NO: 8. In some embodiments, the $V_H$ comprises an amino acid sequence that is 100% identical to SEQ ID NO: 8.

Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FAS™, and SSEARCH) (for sequence alignment and sequence similarity searches). Sequence alignment algorithms also are disclosed in, for example, Altschul et al., *J. Molecular Biol.,* 215(3): 403-410 (1990), Beigert et al., *Proc. Natd. Acad. Sci. USA,* 106(10): 3770-3775 (2009), Durbin et al., eds., *Biological Sequence Analysis: Probabilistic Models of Proteins andNucleic Acids*, Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences*, Cambridge University Press, Cambridge UK (1997)).

As would be recognized by one of ordinary skill in the art based on the present disclosure, one or more amino acids of the aforementioned anti-hCD30 antibodies, or antigen fragments thereof, can be replaced or substituted with a different amino acid. An amino acid "replacement" or "substitution" refers to the replacement of one amino acid at a given position or residue by another amino acid at the same position or residue within a polypeptide sequence. Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg). Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine. Aromatic amino acids may be sub-divided into two sub-groups: the "nitrogen ring sub-group" consisting of histidine and tryptophan and the "phenyl sub-group" consisting of phenylalanine and tyrosine.

The amino acid replacement or substitution can be conservative, semi-conservative, or non-conservative. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure. Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —NH$_2$ can be maintained. "Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

In addition, one or more amino acids can be inserted into the anti-hCD30 antibodies, or antigen-binding fragments thereof (e.g., insertion into the heavy and/or light chain variable region amino acid sequence). Any number of any suitable amino acids can be inserted into the amino acid sequence of the antibody or antigen-binding fragment thereof. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the antibody or antigen-binding fragment thereof. For example, 1-10 amino acids (e.g., 1, 2, 3, 4, 5, 6, 7, 8, 9, or 10 amino acids) may be inserted into the amino acid sequence of the monoclonal antibody or antigen-binding fragment thereof. In this respect, the amino acid(s) can be inserted into antibody or antigen-binding fragment thereof in any suitable location. Preferably, the amino acid(s) are inserted into a CDR (e.g., CDR1, CDR2, or CDR3) of the antibody or antigen-binding fragment thereof.

The amino acid sequences of an anti-hCD30 antibody, or antigen-binding fragments thereof, are not limited to the specific amino acid sequences described herein. Indeed, an anti-hCD30 antibody or antigen-binding fragment thereof can comprise any heavy chain polypeptide or light chain polypeptide that competes with the anti-hCD30 antibodies or antigen-binding fragments thereof for conformational binding to hCD30. Antibody competition can be assayed using routine peptide competition assays such as, for example, ELISA, Western blot, or immunohistochemistry methods (see, e.g., U.S. Pat. Nos. 4,828,981 and 8,568,992; and Braitbard et al., *Proteome Sci.*, 4: 12 (2006)).

An anti-hCD30 antibody of the present disclosure may be a whole antibody, or an antigen-binding fragment of a whole antibody. As defined herein, antigen-binding antibody fragments encompassed by the present disclosure include, but are not limited to, F(ab')$_2$, Fab', Fab, Fv, scFv, dsFv, dAb, and single chain binding polypeptides. Antibody fragments and their therapeutic utility are further described in, e.g., Nelson, A. L., MAbs. 2010 January-February; 2(1): 77-83; Joosten et al., Microbial Cell Factories volume 2, Article number: 1 (2003); and Bates A, Power CA., Antibodies (Basel). 2019; 8(2):28; doi:10.3390/antib8020028). In some embodiments, the anti-hCD30 antigen-binding fragment is a single-chain variable fragment (scFv), which is an engineered antibody generated by the fusion of the heavy ($V_H$) and light chains ($V_L$) of immunoglobulins through a short polypeptide linker. Single chain variable domain (Fv) fragments (scFv) are used in the art in a variety of clinical and therapeutic applications, primarily due to their improved pharmacokinetic properties as compared to the parent monoclonal antibodies and the relative ease of producing them in large quantities at low cost (Monnier et al., Antibodies 2013, 2(2), 193-208; doi.org/10.3390/antib2020193; and Safdari et al., Mol Med. 2016; 22: 258-270.

An anti-hCD30 antibody of the present disclosure may be a diabody. Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003). An anti-hCD30 antibody of the present disclosure may be a single-domain antibody (sdAb), also referred to as a nanobody or llamabody, which is an antibody fragment that comprises a single monomeric variable antibody domain ($V_H$H). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). Antibody fragments can be made by various techniques, including but not limited to proteolytic digestion of an intact antibody as well as production by recombinant host cells (e.g., *E. coli* or phage), as described herein.

In other embodiments, the anti-hCD30 antibody is a whole antibody. As defined herein, a whole antibody comprises two identical copies of a heavy (H) chain polypeptide and two identical copies of a light (L) chain polypeptide. Each of the heavy chains contains one N-terminal variable ($V_H$) region and three C-terminal constant ($C_{H1}$, $C_{H2}$, and $C_{H3}$) regions, and each light chain contains one N-terminal variable ($V_L$) region and one C-terminal constant ($C_L$). The heavy chain C-terminal constant region contains the fragment crystallizable (Fc) domain, which determines antibody class and is responsible for humoral and cellular effector functions. Antibodies are divided into five major classes (or "isotypes"), IgG, IgM, IgA, IgD and IgE, which differ in their function in the immune system. IgGs are the most abundant immunoglobulins in the blood, representing 60% of total serum antibodies in humans. IgG antibodies may be subclassified as IgG1, IgG2, IgG3, and IgG4, named in order of their abundance in serum (IgG1 being the most abundant) (Vidarsson et al., Frontiers in Immunology. 5: 520 (2014)). A whole anti-hCD30 monoclonal antibody described herein may be of any suitable class and/or subclass. In some embodiments, the monoclonal antibody is of class IgG (e.g., IgG1, IgG2, IgG3, or IgG4). For example, the monoclonal antibody may be an IgG1 antibody.

The present disclosure also provides mixtures comprising one or more of the antigen-binding affinity reagents described herein. The mixture can be a homogenous mixture or solution, or the mixture can be a heterogenous mixture or solution. The mixture can include a single type of affinity reagent, or it can include more than one type of affinity reagent. For example, a mixture of one or more of the antigen-binding affinity reagents of the present disclosure can be a mixture of monoclonal antibodies, polyclonal antibodies, humanized antibodies, chimeric antibodies, or single-domain antibodies, including any fragments thereof. In another embodiment, a mixture of antigen-binding affinity reagents of the present disclosure can include two or more different monoclonal antibodies, polyclonal antibodies (e.g., combination of different polyclonal antibody mixtures), humanized antibodies, chimeric antibodies, and/or single-domain antibodies, including any combination thereof. The mixture can be a purified mixture of the antigen-binding affinity reagents of the present disclosure or a non-purified mixture of the antigen-binding affinity reagents of the present disclosure.

As discussed above, the Fc domain mediates several effector functions of antibodies, such as binding to receptors on target cells and complement fixation (triggering effector functions that eliminate the antigen). In some embodiments, the Fc domain may be modified or engineered to alter its effector functions. For example, Fc domains may be modified to improve antibody-dependent cellular cytotoxicity (ADCC) and antibody-dependent cellular phagocytosis (ADCP), and to control serum half-life. In some embodiments, the Fc domain of the anti-hCD30 antibody may be engineered to modulate affinity for an Fc receptor, such as Fcγ receptors (FcγRs) and the neonatal Fc receptor (FcRn). Indeed, optimization of the interactions between antibodies and FcγRs has emerged as a promising approach for enhancing the activity of therapeutic antibodies for the treatment of various diseases (Mimoto et al., Curr. Pharm. Biotechnol. 17, 1298-1314 (2016); Lazar et al., Proc. Natl Acad. Sci. USA 103, 4005-4010 (2006); Richards et al., Mol. Cancer Ther. 7, 2517-2527 (2008); Nordstrom et al., Breast Cancer Res. 13, R123 (2011); and Kang, T. H., Jung, S. T., Exp Mol Med 51, 1-9 (2019)). The Fc domain also may be modified to improve serum half-life, e.g., by engineering IgG Fc for higher FcRn binding (Zalevsky et al., Nat. Biotechnol. 28, 157-159 (2010); and Dall'Acqua et al., J. Immunol. 169, 5171-5180 (2002)). In other embodiments, the Fc domain may be modified to create monovalency or antibody bispecificity for improving therapeutic potency. For example, an Fc domain may be generated that does not form a homodimer but remains as a soluble monomer, mFc, that exhibits high affinity for FcγRI but no detectable binding to FcγRIIIa. In other embodiments, a heterodimeric Fc domain may be generated to obtain bispecific properties for antigen binding to circumvent homodimer formation. Engineered Fc domains may be generated by inducing point mutations or by modifying glycosylation of the Fc domain (Saunders, K. O., Front Immunol. 2019; 10:1296; Kelley, R. F., Meng, Y. G., Liu et al., J Biol Chem. 2014; 289:3571-90; Monnet et al., MAbs. 2014; 6:422-36; Li et al., Proc Natl Acad Sci USA. 2017; 114:3485-90; and Lin et al., Proc Natl Acad Sci USA. 2015; 112:10611-6; Kang and Jung, supra).

Multispecific Anti-hCD30 Antibodies

As described above, the anti-hCD30 antibodies of the present disclosure can be a monoclonal antibody, a human antibody, a humanized antibody, and/or a chimeric antibody. In some embodiments, the antibody is a fragment selected from the group consisting of Fab, Fab-C, Fab'-SH, Fv, scFv, (Fab')$_2$ fragments, and V$_H$H fragments. In some embodiments, the anti-hCD30 antibody is a monospecific antibody. In some embodiments, the anti-hCD30 antibody is a bispecific antibody. In some embodiments, the anti-hCD30 antibody comprises two or more single-domain antibodies that form a bivalent antibody, a trivalent antibody, or a tetravalent antibody that recognizes different epitopes on the same or different antigens.

In some embodiments, an anti-hCD30 antibody provided herein is a chimeric antibody. Certain chimeric antibodies are described, for example, in U.S. Pat. No. 4,816,567; and Morrison et al., *Proc. Natl. Acad. Sci. USA.* 81:6851-6855 (1984). In one example, a chimeric antibody comprises a non-human variable region (e.g., a variable domain derived from a mouse, rat, hamster, rabbit, or non-human primate, such as a monkey) and a human constant domain. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which hypervariable regions (HVRs), for example, CDRs, (or portions thereof) are derived from a non-human antibody, and FRs (or portions thereof) are derived from human antibody sequences. A humanized antibody optionally will also comprise at least a portion of a human constant region. In some embodiments, some framework (FR) residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, for example, in Almagro and Fransson, *Front. Biosci.* 13:1619-1633 (2008), and are further described, for example, in Riechmann et al., *Nature* 332:323-329 (1988); Queen et al., *Proc. Nat'l Acad. Sci.* USA 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

In accordance with the above embodiments, an anti-hCD30 antibody of the present disclosure can be made into bivalent, trivalent, or tetravalent formats. For example, an anti-hCD30 antibody of the present disclosure can be a bivalent, bispecific antibody with heteromeric heavy chains (e.g., Triomab, knobs-into-holes (KIH), Duobody, etc). An anti-hCD30 antibody of the present disclosure can be a tetravalent multispecific antibody comprised of IgGs with other binding domains fused to either the N- or C-termini of either the heavy or light chains (e.g., dual variable domain [DVD], IgG-scFv fusion, Mabtyrin (IgG with non-antibody binding scaffold "centyrin" fused to C-terminal end of heavy chains). An anti-hCD30 antibody of the present disclosure can be comprised of IgGs to which additional antigen combining sites have been added within the structure (e.g., two-in-one antibodies, MAT "Modular Antibody Technology" platform from F-Star). An anti-hCD30 antibody of the present disclosure can be an engineered antibody fragment linked by short peptide linkers which can be made into bivalent, trivalent, or tetravalent formats addressing two to three targets (e.g., bispecific T-cell engager (BiTE), Nanobody platform, dual-affinity re-targeting (DART) antibodies, "tandem antibody" structures (TandAbs)). And an anti-hCD30 antibody of the present disclosure can be comprised of chemically coupled IgGs.

Functional Characteristics of Anti-hCD30 Antibodies

In accordance with the above embodiments, the present disclosure provides anti-hCD30 antibodies comprising various functional characteristics. In some embodiments, the anti-hCD30 antibodies described herein bind an antigen on hCD30 (SEQ ID NO: 9), or a variant or isoform thereof, via interaction with its antigenic determinants (epitopes).

In some embodiments, the anti-hCD30 antibody binds hCD30 with a $K_D$ of about 5 nM or lower.

In some embodiments, the antibody does not cross-react with mCD30.

Polypeptides and Expression Vectors

Embodiments of the present disclosure also include a polynucleotide encoding any of the anti-hCD30 antibodies of the present disclosure, including polynucleotides comprising various degrees of nucleic acid sequence identity, as would be recognized by one of ordinary skill in the art based on the present disclosure.

In accordance with these embodiments, the present disclosure includes an expression vector comprising any of the polynucleotides encoding an anti-hCD30 antibody of the present disclosure. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual,* 4th edition, Cold Spring Harbor Press, Cold Spring Harbor, N.Y. (2012), and Ausubel et al., *Current Protocols in Molecular Biology,* Greene Publishing Associates and John Wiley & Sons, New York, N.Y. (1994)).

In addition to the nucleic acid encoding an anti-hCD30 antibody or antigen-binding fragment thereof, the vector desirably comprises expression control sequences, such as promoters, enhancers, polyadenylation signals, transcription terminators, internal ribosome entry sites (IRES), and the like, that provide for the expression of the antibody-encoding nucleic sequence in a host cell. Exemplary expression control sequences are known in the art and described in, for example, Goeddel, *Gene Expression Technology: Methods in Enzymology,* Vol. 185, Academic Press, San Diego, Calif. (1990).

A vector comprising a nucleic acid sequence encoding an anti-hCD30 antibody or antigen-binding fragment thereof may be introduced into a host cell that is capable of expressing the polypeptides encoded thereby, including any suitable prokaryotic or eukaryotic cell. Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Erwinia*. Particularly useful prokaryotic cells include the various strains of *Escherichia coli* (e.g., K12, 1113101 (ATCC No. 33694), DH5a, DH10, MC1061 (ATCC No. 53338), and CC102). Suitable eukaryotic cells are known in the art and include, for example, yeast cells, insect cells, and mammalian cells. Examples of suitable yeast cells include those from the genera *Hansenula, Kluyveromyces, Pichia, Rhinosporidium, Saccharomyces*, and *Schizosaccharomyces*. Suitable insect cells include Sf-9 and HIS cells (Invitrogen, Carlsbad, Calif) and are described in, for example, Kitts et al., *Biotechniques*, 14: 810-817 (1993); Lucklow, *Curr. Opin. Biotechnol.*, 4: 564-572 (1993); and Lucklow et al., *J. Virol.*, 67: 4566-4579 (1993). Examples of suitable mammalian cells include, but are not limited to, Chinese hamster ovary cells (CHO) (ATCC No. CCL61), CHO DHFR-cells (Urlaub et al., *Proc. Natl. Acad. Sci. USA*, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants also are suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of such cells are well known in the art (see, e.g., Ausubel et al., eds., *ShortProtocols inMolecular Biology*, 5th ed., John Wiley & Sons, Inc., Hoboken, N.J. (2002)). Preferably, the mammalian cell is a human cell.

In some embodiments, the vector can include means for attaching a detection moiety to an anti-hCD30 antibody of the present disclosure. In some embodiments, the vector can include means for attaching a purification moiety to an anti-hCD30 antibody of the present disclosure. Exemplary detection and/or purification moieties/tags that can be coupled to an anti-hCD30 antibody of the present disclosure includes, but is not limited to, hemagglutinin (HA), c-Myc, V5, DYKDDDDK, His tag (e.g., 6x-HIS), Glutathione S-Transferase (GST), Maltose Binding Protein (MBP), a fluorophore (e.g., Green Fluorescent Protein (GFP), Red Fluorescent Protein (RFP), mCherry, a chromophore, and/or a luminescent peptide (e.g., luciferase).

An anti-hCD30 antibody or antigen-binding fragment, described herein can be used in diagnostic or research applications. Research applications include, for example, methods that utilize the anti-hCD30 antibody and a label to detect hCD30 in a sample, e.g., in a human body fluid or in a cell or tissue extract. The anti-hCD30 antibody or antigen-binding fragment thereof may be employed in any suitable assay for measuring hCD30 in a sample for diagnostic and/or research purposes. Such assays include, but are not limited to, sandwich immunoassays, enzyme immunoassays (EIA), enzyme-linked immunosorbent assays (ELISA), lateral flow assays, competitive inhibition immunoassays (e.g., forward and reverse), competitive binding assays, Forster resonance energy transfer (FRET), one-step antibody detection assays, single molecule detection assays, radioimmunoassays (RIA), and FACS. Such methods are disclosed in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792; and Adamczyk et al., *Anal. Chim. Acta*, 579(1): 61-67 (2006).

The anti-hCD30 antibody or antigen-binding fragment thereof can be provided in a kit, e.g., a packaged combination of reagents in predetermined amounts with instructions for performing an assay using the antibody (e.g., an assay that detects hCD30). As such, the disclosure provides a kit comprising the antibody or antigen-binding fragment described herein and instructions for use thereof. The instructions can be in paper form or computer-readable form, such as a disk, CD, DVD, etc. Alternatively, or additionally, the kit can comprise a calibrator or control, and/or at least one container (e.g., tube, microtiter plates, or strips) for conducting an assay, and/or a buffer, such as an assay buffer or a wash buffer. Ideally, the kit comprises all components, i.e., reagents, standards, buffers, diluents, etc., which are necessary to perform the assay. Other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

The following examples further illustrate the various embodiments of the present disclosure but should not be construed as in any way limiting its scope.

EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Detection of Human CD30 in Jurkat Human Cell Line by Flow Cytometry

Jurkat human acute T cell leukemia cell line (Clone E6-1, ATCC Catalog #TIB-152) was stained with Mouse Anti-Human CD30 Monoclonal Antibody (Clone 81316.11, filled histogram) or isotype control antibody (Catalog #MAB002, open histogram), followed by Phycoerythrin-conjugated Anti-Mouse IgG Secondary Antibody (Catalog #F0102B).

Jurkat cells were harvested and washed two times in 2 mL of 1x flow staining buffer (FC001). The cells were resuspended in 1x flow staining buffer to a concentration of ~1.0×10⁶ cells/mL. About 90 µL of the cell suspension was added to each flow tube. About 10 µL of either 25 µg/mL Msxh CD30 or MsIgG1 was added to the appropriate tube, and the tubes were vortexed and then incubated for 20 minutes at room temperature. Cells were washed two times in 2 mL of 1× flow staining buffer. About 10 µL of goat anti-Mouse IgG PE secondary antibody was added to each tube, vortexed, and then incubated in the dark for 20 minutes at room temperature. Cells were washed two times in 2 mL of 1× flow staining buffer. 100 µL of 2× Sytox Blue Dead Cell Stain (ThermoFisher, S34857) was added and the cells were analyzed by flow cytometry.

Example 2

Surface plasmon resonance binding of the anti-hCD30 antibody Surface plasmon resonance binding of the anti-hCD30 antibody (employed here as the surface immobilized ligand) to recombinant human CD30 protein (employed here as the solution phase analyte). The four traces show (from highest to lowest) the binding response to 40 nM, 8 nM, 1.6 nM, and 0.32 nM concentrations of the hCD30 analyte, respectively. The experimental data was double referenced by removing the trace background binding responses measured in the absence of either ligand or analyte. The reference subtracted experimental data was fit using a 1:1 ligand-analyte Langmuir kinetics binding model. The values for the best-fit kinetic rate constants of association ($k_{on}$) and dissociation ($k_{off}$), along with the equilibrium dissociation constant are shown in the inset (top right).

Sequences

The various amino acid sequences and nucleic acid sequences referenced herein are provided below.

TABLE 1

Anti-hCD30 antibody sequences.

| SEQ ID NO: | Antibody Name: | Descriptor: | Sequence: |
|---|---|---|---|
| 1 | hCD30 | HCDR1 | GFSLTSYGVH |
| 2 | hCD30 | HCDR2 | WLGVIWAGETINYNLALMS |
| 3 | hCD30 | HCDR3 | ARDQGEYGNYGWYFDV |
| 4 | hCD30 | LCDR1 | SASQGISNYLNWY |
| 5 | hCD30 | LCDR2 | LLIYYTSSLHS |
| 6 | hCD30 | LCDR3 | QHYSKLPPT |
| 7 | hCD30 | VH | QVQLKESGPGLVAPSQSLSITCTVSGFSLTSYGV HWVRQPPGKGLEWLGVIWAGETINYNLALMS RLSISKDNSKSQVFLKMNSLQTEDTAMYYCAR DQGEYGNYGWYFDVWGAGTTVTVSS |
| 8 | hCD30 | VL | DIQMTQTTSSLSASLGDRVTISCSASQGISNYLN WYQQKPDGTVKLLIYYTSSLHSGVPSRFSGSGS GTDYSLTISNLEPEDIATYYCQHYSKLPPTFGGG TKLEIKRA |

Human CD30 isoform 1 (UniProt Accession No. P28908-1): MRVLLAALGLLFLGALRAFPQDRPFEDTCHGNP-SHYYDKAVRRCCYRCPMGLFPTQQC PQRPTDCRKQ-CEPDYYLDEADRCTACVTCSRDDLVEKTPCAWNSSRVCE-CRPGMFCST SAVNSCARCFFHSVCPAGMIVKFPGTAQKNTV-CEPASPGVSPACASPENCKEPSSGTIPQ AKPTPVSPATSSASTMPVRGGTRLAQEAASKLTRAP-DSPSSVGRPSSDPGLSPTQPCPEGS GDCRKQ-CEPDYYLDEAGRCTACVSCSRDDLVEKTP-CAWNSSRTCECRPGMICATSATN SCARCVPYPICAAETVTKPQDMAEKDTTFEAP-PLGTQPDCNPTPENGEAPASTSPTQSLL VDSQASKTLPIPT-SAPVALSSTGKPVLDAGPVLFWVILVLVVVVGS-SAFLLCHRRACRKR IRQKLHLCYPVQTSQPKLEL-VDSRPRRSSTQLRSGASVTEPVAEERGLMSQPL-METCHSV GAAYLESLPLQDASPAGGPSSPRDL-PEPRVSTEHTNNKIEKIYIMKADTVIVGTVKAELPE GRGLAGPAEPELEEELEADHTPHYPEQETEP-PLGSCSDVMLSVEEEGKEDPLPTAASGK (SEQ ID NO: 9).

Human CD30 isoform 2 (UniProt Accession No. P28908-2): MSQPLMETCHSVGAAYLESLPLQ-DASPAGGPSSPRDLPEPRVSTEHTNNKIEKIYIMKAD TVIVGTVKAELPEGRGLAGPAEPELEEELEADHTP-HYPEQETEPPLGSCSDVMLSVEEEG KEDPLPTAASGK (SEQ ID NO: 10).

Human CD30 isoform 3 (UniProt Accession No. P28908-3): MFCSTSAVNSCARCFFHSVCPAG-MIVKFPGTAQKNTVCEPASPGVSPACASPENCKEPSS GTIPQAKPTPVSPATSSASTMPVRGGTRLAQEAASKL-TRAPDSPSSVGRPSSDPGLSPTQP CPEGSGDCRKQ-CEPDYYLDEAGRCTACVSCSRDDLVEKTP-CAWNSSRTCECRPGMICA TSATNSCARCVPYPICAAETVTKPQDMAEKDTTFE-APPLGTQPDCNPTPENGEAPASTSP TQSLL-VDSQASKTLPIPT-SAPVALSSTGKPVLDAGPVLFWVILVLVVVVGSSA-FLLCHRR ACRKRIRQKLHLCYPVQTSQPKLELVDSR-PRRSSTLRSGASVTEPVAEERGLMSQPLMET CHSVGAAYLESLPLQDASPAGGPSSPRDL-PEPRVSTEHTNNKIEKIYIMKADTVIVGTVK AELPE-GRGLAGPAEPELEEELEADHTPHYPEQETEP-PLGSCSDVMLSVEEEGKEDPLPTAASGK (SEQ ID NO: 11).

The use of the terms "a" and "an" and "the" and "at least one" and similar referents in the context of describing the embodiments of the present disclosure (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the various embodiments of the present disclosure and does not pose a limitation on the scope of these embodiment unless otherwise claimed. No language in the specification should be construed as indicating any non-claimed element as essential to the practice of the various embodiments of the present disclosure.

Various embodiments of the present disclosure are described herein. Variations of those embodiments may become apparent to those of ordinary skill in the art upon reading the foregoing description. The inventors expect skilled artisans to employ such variations as appropriate, and the inventors intend for the various embodiments of the present disclosure to be practiced otherwise than as specifically described herein. Accordingly, embodiments of the present disclosure include all modifications and equivalents of the subject matter recited in the claims appended hereto as permitted by applicable law. Moreover, any combination of the above-described elements in all possible variations thereof is encompassed by the various embodiments of the present disclosure unless otherwise indicated herein or otherwise clearly contradicted by context.

SEQUENCE LISTING

```
Sequence total quantity: 11
SEQ ID NO: 1            moltype = AA  length = 10
FEATURE                 Location/Qualifiers
source                  1..10
                        mol_type = protein
                        organism = Synthetic construct
SEQUENCE: 1
GFSLTSYGVH                                                                10

SEQ ID NO: 2            moltype = AA  length = 19
FEATURE                 Location/Qualifiers
source                  1..19
                        mol_type = protein
                        organism = Synthetic construct
SEQUENCE: 2
WLGVIWAGET INYNLALMS                                                      19

SEQ ID NO: 3            moltype = AA  length = 16
FEATURE                 Location/Qualifiers
source                  1..16
                        mol_type = protein
                        organism = Synthetic construct
SEQUENCE: 3
ARDQGEYGNY GWYFDV                                                         16

SEQ ID NO: 4            moltype = AA  length = 13
FEATURE                 Location/Qualifiers
source                  1..13
                        mol_type = protein
                        organism = Synthetic construct
SEQUENCE: 4
SASQGISNYL NWY                                                            13

SEQ ID NO: 5            moltype = AA  length = 11
FEATURE                 Location/Qualifiers
source                  1..11
                        mol_type = protein
                        organism = Synthetic construct
SEQUENCE: 5
LLIYYTSSLH S                                                              11

SEQ ID NO: 6            moltype = AA  length = 9
FEATURE                 Location/Qualifiers
source                  1..9
                        mol_type = protein
                        organism = Synthetic construct
SEQUENCE: 6
QHYSKLPPT                                                                 9

SEQ ID NO: 7            moltype = AA  length = 122
FEATURE                 Location/Qualifiers
source                  1..122
                        mol_type = protein
                        organism = Synthetic construct
```

```
SEQUENCE: 7
QVQLKESGPG LVAPSQSLSI TCTVSGFSLT SYGVHWVRQP PGKGLEWLGV IWAGETINYN   60
LALMSRLSIS KDNSKSQVFL KMNSLQTEDT AMYYCARDQG EYGNYGWYFD VWGAGTTVTV  120
SS                                                                122

SEQ ID NO: 8            moltype = AA  length = 109
FEATURE                 Location/Qualifiers
source                  1..109
                        mol_type = protein
                        organism = Synthetic construct
SEQUENCE: 8
DIQMTQTTSS LSASLGDRVT ISCSASQGIS NYLNWYQQKP DGTVKLLIYY TSSLHSGVPS   60
RFSGSGSGTD YSLTISNLEP EDIATYYCQH YSKLPPTFGG GTKLEIKRA             109

SEQ ID NO: 9            moltype = AA  length = 595
FEATURE                 Location/Qualifiers
source                  1..595
                        mol_type = protein
                        organism = Synthetic construct
SEQUENCE: 9
MRVLLAALGL LFLGALRAFP QDRPFEDTCH GNPSHYYDKA VRRCCYRCPM GLFPTQQCPQ   60
RPTDCRKQCE PDYYLDEADR CTACVTCSRD DLVEKTPCAW NSSRVCECRP GMFCSTSAVN  120
SCARCFFHSV CPAGMIVKFP GTAQKNTVCE PASPGVSPAC ASPENCKEPS SGTIPQAKPT  180
PVSPATSSAS TMPVRGGTRL AQEAASKLTR APDSPSSVGR PSSDPGLSPT QPCPEGSGDC  240
RKQCEPDYYL DEAGRCTACV SCSRDDLVEK TPCAWNSSRT CECRPGMICA TSATNSCARC  300
VPYPICAAET VTKPQDMAEK DTTFEAPPLG TQPDCNPTPE NGEAPASTSP TQSLLVDSQA  360
SKTLPIPTSA PVALSSTGKP VLDAGPVLFW VILVLVVVG SSAFLLCHRR ACRKRIRQKL  420
HLCYPVQTSQ PKLELVDSRP RRSSTQLRSG ASVTEPVAEE RGLMSQPLME TCHSVGAAYL  480
ESLPLQDASP AGGPSSPRDL PEPRVSTEHT NNKIEKIYIM KADTVIVGTV KAELPEGRGL  540
AGPAEPELEE ELEADHTPHY PEQETEPPLG SCSDVMLSVE EEGKEDPLPT AASGK       595

SEQ ID NO: 10           moltype = AA  length = 132
FEATURE                 Location/Qualifiers
source                  1..132
                        mol_type = protein
                        organism = Synthetic construct
SEQUENCE: 10
MSQPLMETCH SVGAAYLESL PLQDASPAGG PSSPRDLPEP RVSTEHTNNK IEKIYIMKAD   60
TVIVGTVKAE LPEGRGLAGP AEPELEEELE ADHTPHYPEQ ETEPPLGSCS DVMLSVEEEG  120
KEDPLPTAAS GK                                                     132

SEQ ID NO: 11           moltype = AA  length = 483
FEATURE                 Location/Qualifiers
source                  1..483
                        mol_type = protein
                        organism = Synthetic construct
SEQUENCE: 11
MFCSTSAVNS CARCFFHSVC PAGMIVKFPG TAQKNTVCEP ASPGVSPACA SPENCKEPSS   60
GTIPQAKPTP VSPATSSAST MPVRGGTRLA QEAASKLTRA PDSPSSVGRP SSDPGLSPTQ  120
PCPEGSGDCR KQCEPDYYLD EAGRCTACVS CSRDDLVEKT PCAWNSSRTC ECRPGMICAT  180
SATNSCARCV PYPICAAETV TKPQDMAEKD TTFEAPPLGT QPDCNPTPEN GEAPASTSPT  240
QSLLVDSQAS KTLPIPTSAP VALSSTGKPV LDAGPVLFWV ILVLVVVGS SAFLLCHRRA  300
CRKRIRQKLH LCYPVQTSQP KLELVDSRPR RSSTLRSGAS VTEPVAEERG LMSQPLMETC  360
HSVGAAYLES LPLQDASPAG GPSSPRDLPE PRVSTEHTNN KIEKIYIMKA DTVIVGTVKA  420
ELPEGRGLAG PAEPELEEEL EADHTPHYPE QETEPPLGSC SDVMLSVEEE GKEDPLPTAA  480
SGK                                                               483
```

What is claimed is:

1. An antibody, or an antigen-binding fragment thereof, directed against human CD30 (hCD30) comprising:

a heavy chain variable region (V$_H$) comprising complementarity determining regions (CDRs) HCDR1, HCDR2, and HCDR3; wherein the HCDR1 comprises SEQ ID NO: 1, the HCDR2 comprises SEQ ID NO: 2, and the HCDR3 comprises SEQ ID NO: 3; and a light chain variable region (V) comprising complementarity determining regions (CDRs) LCDR1, LCDR2, and LCDR3; wherein the LCDR1 comprises SEQ ID NO: 4, the LCDR2 comprises SEQ ID NO: 5, the LCDR3 comprises SEQ ID NO: 6.

2. The CD30 antibody or antibody fragment of claim 1, wherein the antibody is a monoclonal antibody, a humanized antibody, or a chimeric antibody.

3. The hCD30 antibody or antibody fragment of claim 1, wherein the antibody fragment is selected from the group consisting of Fab, Fab-C, Fab'-SH, Fv, scFv, and (Fab')$_2$.

4. The hCD30 antibody or antibody fragment of claim 1, wherein the antibody or antibody fragment binds hCD30 with a K$_D$ of about 5 nM or lower.

5. The hCD30 antibody or antibody fragment of claim 1, wherein the antibody or antibody fragment does not cross-react with mouse CD30 (mCD30).

6. The hCD30 antibody or antibody fragment of claim 1, wherein the antibody or antibody fragment comprises a detection moiety or a purification moiety.

7. The hCD30 antibody or antibody fragment of claim 1, wherein the antibody or antibody fragment binds an epitope from a hCD30 polypeptide having an amino acid sequence of SEQ ID NO: 9.

8. The hCD30 antibody or antibody fragment claim 1, wherein the antibody or antibody fragment binds an epitope from a hCD30 polypeptide having an amino acid sequence of SEQ ID NO: 10.

9. The hCD30 antibody or antibody fragment of claim 1, wherein the antibody or antibody fragment binds an epitope from a hCD30 polypeptide having an amino acid sequence of SEQ ID NO: 11.

10. A polynucleotide comprising a nucleic acid sequence encoding the hCD30 antibody or antibody fragment of claim 1.

* * * * *